(12) United States Patent
Fröjd (10) Patent No.: US 8,475,434 B2
(45) Date of Patent: Jul. 2, 2013

(54) URINARY CATHETER WITH ONE WAY CHECK VALVE

(75) Inventor: Göran Fröjd, Göteborg (SE)

(73) Assignee: Astra Tech AB, Mölndal (SE)

( * ) Notice: Subject to any disclaimer, the term of this patent is extended or adjusted under 35 U.S.C. 154(b) by 235 days.

(21) Appl. No.: 11/892,900

(22) Filed: Aug. 28, 2007

(65) Prior Publication Data

US 2008/0051763 A1 Feb. 28, 2008

Related U.S. Application Data

(60) Provisional application No. 60/840,465, filed on Aug. 28, 2006.

(51) Int. Cl.
*A61M 27/00* (2006.01)
*A61M 39/24* (2006.01)

(52) U.S. Cl.
USPC .......................................... 604/544; 604/323

(58) Field of Classification Search
USPC ........................... 604/540, 544, 328; 206/364
See application file for complete search history.

(56) References Cited

U.S. PATENT DOCUMENTS

| | | | | |
|---|---|---|---|---|
| 4,828,554 A | * | 5/1989 | Griffin | 604/350 |
| 6,090,075 A | * | 7/2000 | House | 604/172 |
| 6,352,526 B1 | * | 3/2002 | Cawood | 604/323 |
| 6,409,717 B1 | * | 6/2002 | Israelsson et al. | 604/544 |
| 6,634,498 B2 | * | 10/2003 | Kayerød et al. | 206/364 |
| 6,736,805 B2 | * | 5/2004 | Israelsson et al. | 604/544 |
| 6,849,070 B1 | * | 2/2005 | Hansen et al. | 604/544 |
| 7,066,912 B2 | * | 6/2006 | Nestenborg et al. | 604/171 |
| 7,087,048 B2 | * | 8/2006 | Israelsson et al. | 604/544 |
| 7,331,949 B2 | * | 2/2008 | Marisi | 604/544 |
| 2003/0083644 A1 | * | 5/2003 | Avaltroni | 604/544 |
| 2003/0130646 A1 | * | 7/2003 | Kubalak et al. | 604/544 |
| 2003/0135231 A1 | | 7/2003 | Goodin et al. | |
| 2006/0079854 A1 | * | 4/2006 | Kay et al. | 604/328 |
| 2007/0149929 A1 | * | 6/2007 | Utas et al. | 604/172 |

FOREIGN PATENT DOCUMENTS

| | | |
|---|---|---|
| EP | 0 208 841 A2 | 1/1987 |
| WO | WO-98/11932 A1 | 3/1998 |
| WO | WO-01/43807 A1 | 6/2001 |

* cited by examiner

*Primary Examiner* — Susan Su
(74) *Attorney, Agent, or Firm* — Birch, Stewart, Kolasch & Birch, LLP (57) ABSTRACT

A catheter and catheter assembly are disclosed comprising a urinary catheter comprising an insertion end, a rearward end, and a one way check valve arrangement. The check valve arrangement comprises a tubular part of a flexible material, connected to the rearward end of the catheter and extending past the rearward end in a direction opposite to the insertion end, thereby substantially limiting the flow through the catheter to a single direction from the insertion end to the rearward end. Hereby, a very effective anti-reflux function is achieved, and at the same time the construction is relatively simple and inexpensive, and does not require any essential modifications of the other parts of the urinary catheter.

34 Claims, 7 Drawing Sheets

URINARY CATHETER WITH ONE WAY CHECK VALVE

This Nonprovisional application claims priority under 35 U.S.C. §119(e) on U.S. Provisional Application No. 60/840,465 filed on Aug. 28, 2006, the entire contents of which are hereby incorporated by reference.

FIELD OF THE INVENTION

The present invention relates to a urinary catheter, a urinary catheter assembly and a method for producing a urinary catheter.

BACKGROUND OF THE INVENTION

Catheters find their use in many different medical applications, such as urinary catheters for bladder drainage. Each catheter is normally pre-packed in a receptacle by the manufacturer, in order to maintain the catheter in a clean and preferably sterile condition.

A urinary catheter in general need to have a lubricant applied to the outer surface thereof to facilitate insertion into the urethra. Especially, for lubrication purposes, a hydrophilic urinary catheter may have a hydrophilic outer surface coating or layer which should be wetted by a fluid such as water for a certain time period prior to insertion of the catheter into the urethra of a patient. In order to facilitate the use and to improve cleanliness of the catheter, the assemblies have in recent years developed to comprise a rupturable wetting fluid pouch or container as well. Such assemblies are disclosed in e.g. WO 97/26937, WO 01/43807 and WO 98/11932.

The purpose of a urinary catheter is to drain out the bladder into which it is inserted, and to this end, the catheter tube is normally at the outside end connected to a collection container or collection bag. However, the possibility exists that, should e.g. the collection container be crushed or raised above the level of the bladder being drained, the drained urine may flow in reverse, and reenter the cavity from which it was drained. This is not only uncomfortable and possibly painful for the patient, but may also cause introduction of bacteria and the like into the bladder. A related problem is that there is a significant risk for spillage through the catheter after the catheterization, when the catheter has been removed from the bladder.

To this end, different types of catheters with check valves arrangement integrated therein have been proposed in the art. For example, such catheters are disclosed in US 2004/0172009, U.S. Pat. Nos. 4,227,533 and 6,682,503. In all these catheters, the check valve arrangement is integrated in the catheter, thereby providing an anti-reflux valve some way along the internal lumen of the catheter. Even though these known catheter may be sufficient for alleviating the above-discussed reflux problems, these known devices are all affected with certain drawbacks. For example, a common problem with all these known devices is that they are relatively complicated and expensive to produce. Consequently, these known solutions will normally not be considered for urinary catheters, and especially not for disposable single-use intermittent catheters. Further, the solutions proposed in the prior art will normally restrict the flow throughput of the catheters. i.e. increasing the flow resistance, thereby making the catheters less effective for their intended use. Still further, the previously known solutions for providing anti-reflux valves in catheters are unsuitable for use in catheters provided with a surface coating, such as a hydrophilic surface coating, since it is difficult to avoid coating building up in the vicinity of the anti-reflux valve during manufacturing, which may affect the valve in a negative fashion.

In addition, urine collection bags with integrated check-valves have been proposed in the past, e.g. in EP 0 185 809. However, such known collection bags are affected with a number of drawbacks. For example, these solutions are not suitable for urinary catheter assemblies where the urine collection bag is integrated in the receptacle accommodating the catheter before use, since the check-valve would then prevent easy and effective activation of the assembly, and would also hinder an effective wetting of a hydrophilic urinary catheter, especially for assemblies comprising a rupturable wetting fluid pouch or container.

Accordingly, there is still a need for an improved catheter assembly which alleviates the above-discussed problems of the prior art.

SUMMARY OF THE INVENTION

It is a general object of the present invention to alleviate the above-discussed problems.

This object is achieved with a urinary catheter, a urinary catheter assembly and a production method according to the appended claims.

According to a first aspect, there is provided a urinary catheter comprising an insertion end, a rearward end, and a one way check valve arrangement. The check valve arrangement comprises a tubular part of a flexible material, said tubular part being connected to the rearward end of the catheter and extending past the rearward end in a direction opposite to the insertion end, thereby substantially limiting the flow through the catheter to a single direction from the insertion end to the rearward end.

By tubular part is in the context of this application to be understood essentially any part presenting a tubular opening over the whole or a part of its length.

By rearward end of the catheter is, in the context of this application, meant the part of the catheter forming the outlet end of the ordinary catheter lumen through the catheter. This rearward end is commonly known as the "connector" of the catheter, since it may be connected to drainage tubing and the like, or as the "outlet end". However, the rearward end need not be the most rearward part of the catheter. Further, the rearward part may be an integrated part of the catheter shaft, or be a separate component connected to said shaft.

With the present invention, the rearwardly extending "hose" provides a simple, but yet effective one-way check valve, in which the flow is essentially unrestricted in an intended first direction, i.e. urine flowing from the bladder, but which effectively restricts any flow in the opposite direction, since the rearward output opening of the check valve arrangement is automatically closed whenever the external pressure, from e.g. surrounding collected urine, increases.

By means of the urinary catheter, the catheter may be pre-manufactured, and the check-valve arrangement provided afterwards, by arranging the tubular part on the rearward part of the catheter. This check-valve arrangement can be arranged on essentially any type of existing urinary catheter. Consequently, the check-valve arrangement of the invention is relatively simple and inexpensive. Further, any coating process or the like used in the manufacturing of the catheter can remain totally unchanged, and without any affection on the check-valve arrangement, since this may be arranged after the coating process. Still further, the flow throughput through the catheter lumen may be maintained essentially not affected, since the check-valve arrangement is arranged behind the catheter lumen, thereby causing essentially no additional flow resistance to the catheter. Additionally, the tubular part may even have an internal diameter being larger than the internal diameter of the lumen. Nonetheless, the check-valve arrangement of the present invention can easily be made to provide adequate anti-reflux properties for the intended use.

Preferably, the tubular part comprises two openings, one of which is sealingly connected to the rearward end of the catheter, and the other presenting an open end opposite to said sealingly connected end. The check valve arrangement preferably has an inlet at its attachment to the rearward end, and an outlet at the opposite end of the tubular part, wherein said inlet remains substantially open for passage of fluids there through, and said outlet being biased to closure after discharge of fluids through said outlet, thereby substantially limiting the flow to a single direction from said inlet to said outlet. However, alternatively, it is e.g. also feasible to have a tubular part comprising several outlet openings.

The tubular part preferably has an elongated form, wherein the length of the tubular part is at least three times the diameter of the rearward end of the catheter, and preferably at least five times said diameter, and most preferably at least ten times said diameter. Further, the tubular part preferably has an elongated form, wherein the length of said tubular part is at least 30 mm, and preferably at least 80 mm. Due to the provision of a certain elongation of the tubular part, sufficiently good anti-reflux capacity may be achieved for essentially any application. The minimum length required for the provision of adequate anti-reflux properties are however dependent on the type of assembly or application in which the catheter is used, the pressures expected to be applied externally to a surrounding fluid, the degree of reflux limitation that is required, etc.

The tubular part of the check valve arrangement preferably has an inner diameter which is at least twice the inner diameter of a lumen of the catheter. Hereby, it is ensured that the check-valve arrangement causes no restriction of the flow through the catheter.

The check valve arrangement may have a perimeter attached along an exterior periphery of the rearward end of the catheter.

The tubular part is preferably connected to said rearward end by means of at least one of the following methods: shrinkage, force fitting, welding and adhesive bonding.

The tubular part may be made of any suitable material, providing the required flexibility. For example this material may be selected from a group consisting of polyurethanes, latex rubbers, other rubbers, polyvinylchloride, other vinyl polymers, polyesters and polyacrylates. In particular, it is preferred to use ethylene-acrylic ester copolymers, such as ethyl-methyl acrylate (EMA) copolymers and ethylene-butyl acrylate (EBA) copolymers, poly ethene or poly propene. The exterior of the rearward end preferably has a frusto-conical shape, wherein the external diameter of said rearward end increases in direction away from the catheter insertion end. This makes the connection of the tubular part to the rearward end of the catheter particularly easy to obtain.

The insertable length of the catheter may be provided with a hydrophilic surface coating providing low-friction surface character of the catheter by treatment with a wetting fluid. However, it is appreciated by those versed in the art that the check-valve arrangement of the present invention may also be used for other types of catheters, having other types of coatings, or having no coating at all.

The tubular part of the check valve arrangement is preferably formed from an plastic material. Further, the wall thickness is preferably less than 0.5 mm, and most preferably less than 0.3 mm, in order to be sufficiently flexible for most suitable materials.

The inner diameter of the tubular part of the check valve arrangement is preferably wider at the outlet than at the inlet, wherein the outlet inner diameter preferably is at least twice the inlet inner diameter. By this, preferably gradual or continuous, widening of the lumen through the check valve arrangement, essentially no additional flow resistance is added to the flow resistance of the ordinary catheter lumen between the forward and rearward end. However, the widths at the outlet and the inlet may also be essentially identical.

According to another aspect of the present invention, there is provided a urinary catheter assembly comprising a urinary catheter and a receptacle, arranged to accommodate said catheter, wherein said catheter comprises an insertion end, a rearward end, and a one way check valve arrangement. The check valve arrangement comprises a tubular part of a flexible material being connected to the rearward end of the catheter, and extending past the rearward end in a direction opposite to the insertion end, thereby substantially limiting the flow to a single direction from the insertion end to the rearward end.

By means of this aspect of the invention, similar advantages are provided as already discussed in view of the previously discussed aspect of the invention.

Preferably, the receptacle is also a urine collection bag. Hereby, the check-valve arrangement prevents or substantially prevents leakage through the catheter after use, and after drainage of the bladder, making the handling and disposal of the urinary catheter assembly significantly easier.

Preferably, the assembly further comprises a wetting fluid, wherein the catheter has on at least part of its surface a hydrophilic surface layer providing low-friction surface character of the device by treatment with said wetting fluid. Most preferably, the assembly presents a storage state in which the wetting fluid is kept separated from the hydrophilic surface layer of the catheter, and an activation state in which the wetting fluid is brought into contact with said hydrophilic surface layer before an intended use of the catheter. For example, the receptacle can comprise a wetting fluid container, containing a wetting fluid and being openable to enable the wetting fluid to be discharged from the wetting fluid container for wetting of the urinary catheter. The receptacle preferably has an elongate pocket, defining a wetting fluid receiving area, which accommodates the insertable length of said urinary catheter. In such an arrangement, the above-discussed check-valve arrangement enables effective wetting of the hydrophilic surface of the urinary catheter, and an essentially unrestricted passage of the wetting fluid into the wetting fluid receiving area.

According to still another aspect of the present invention there is provided a method for manufacturing a urinary catheter with a one way check valve arrangement comprising the steps:

providing a urinary catheter having an insertion end and a rearward end;

providing a tubular part of a flexible material;

connecting said tubular part to said rearward end of the urinary catheter in such a way that the tubular part extends past the rearward end in a direction opposite to the insertion end of the catheter for provision of said check valve arrangement.

By means of this aspect of the invention, similar advantages are provided as already discussed in view of the previously discussed aspects of the invention.

These and other aspects of the inventive concept will be apparent from and elicited with reference to the embodiments described hereinafter.

BRIEF DESCRIPTION OF THE DRAWINGS

By way of example embodiments of the invention will now be described with reference to the accompanying drawings in which.

DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter, the dimensions of the fluid compartments, etc.

Figure 1:
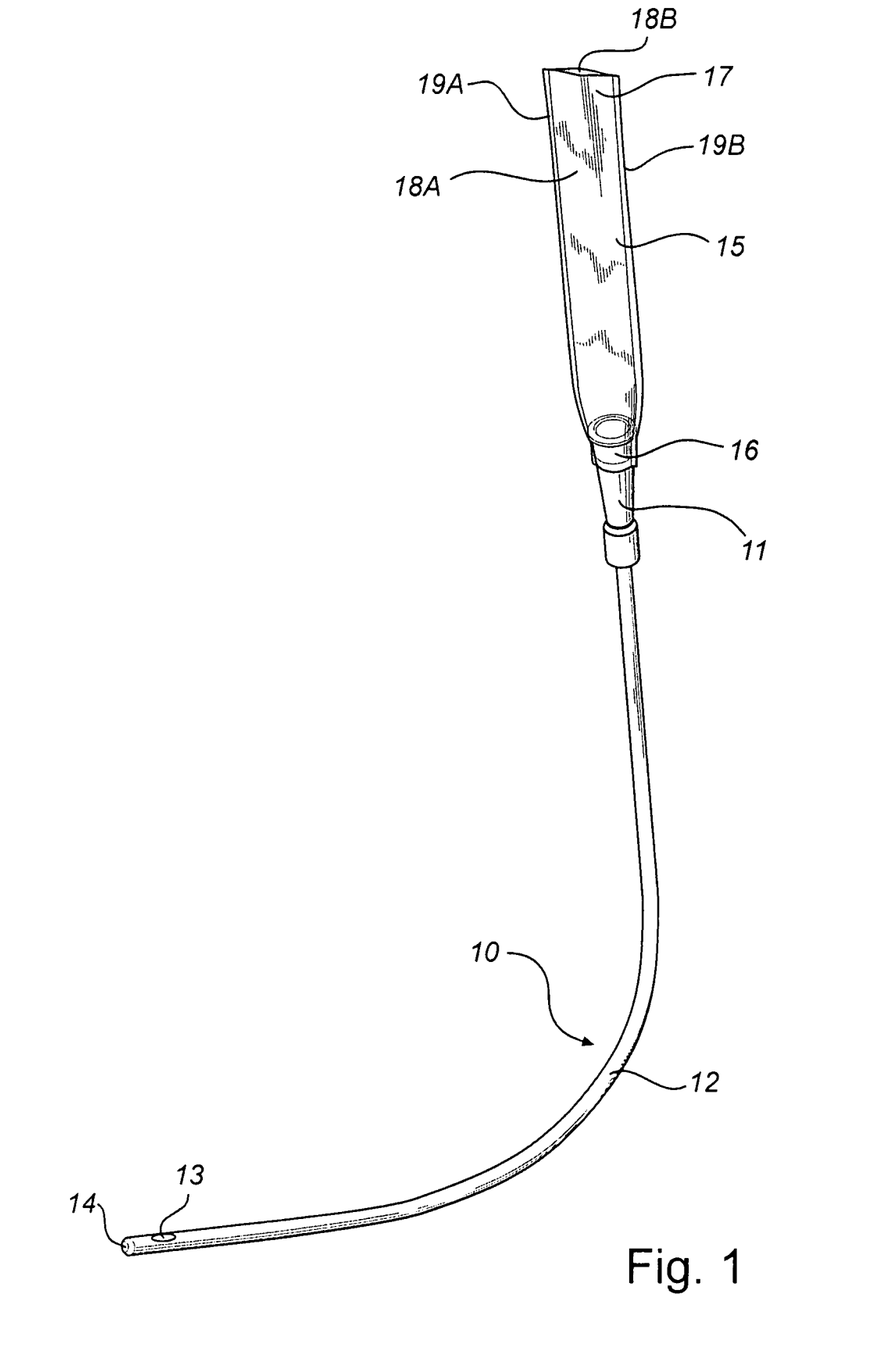
FIG. 1 illustrates a urinary catheter according to one embodiment of the invention.

A catheter 10 as illustrated in the drawings, e.g. in FIG. 1, comprises a flared rearward portion 11 and an elongate shaft or tube 12 projecting forwardly from the rearward portion 11. An open-ended internal lumen (not shown) extends from the rear end of the rearward portion 11 to a drainage aperture 13 in a rounded tip 14 of the elongate tube 12. The rearward portion 11 may function as a connector of the catheter 10, being connectable to other devices, such as a urine collection bag, a drainage tube or the like. Further, the flared rearward portion 11 may sealingly engage with a narrow opening of a receptacle which also functions as a urine collection bag, as is discussed in more detail in the following.

At least a part of the elongate tube 12 forms an insertable length to be inserted through a body opening of the user, such as the urethra in case of a urinary catheter. By insertable length is normally, in the context of a hydrophilic catheter, meant that length of the elongate tube 12 which is coated with a hydrophilic material, for example PVP, and which is insertable into the urethra of the patient. Typically, this will be 80-140 mm for a female patient and 200-350 mm for a male patient. Several different types of hydrophilic polymer coating are feasible, as is per se known in the art. However, a preferred hydrophilic polymer is polyvinylpyrrolidone.

The substrates may be made from any polymer material, which are well-known in the technical field and to which the said hydrophilic polymers adhere, such as polyurethanes, latex rubbers, other rubbers, polyvinylchloride, other vinyl polymers, polyesters and polyacrylates.

Further, the catheter is provided with a one way checkvalve arrangement. This check valve arrangement comprises a tubular part 15 of a flexible material, having one end connected to the rearward part 11 of the catheter, and extending past the rearward end in a direction opposite to the insertion end 14, thereby substantially limiting the flow through the catheter to a single direction from the insertion end to the rearward end. the other presenting an open end opposite to said sealingly connected end. The other end 17 of the tubular part is freely ending, and provides an outlet for the catheter. The inlet 16 of the tubular part 15 remains substantially open for passage of fluids there through at all times, whereas the outlet 17 is biased to closure after discharge of fluids through said outlet from the surrounding fluid, thereby substantially limiting the flow to a single direction from said inlet to said outlet. Thus, when the tubular part 15 is surrounded by collected urine, an increased pressure in the collected fluid will cause the walls of the tubular parts to be pressed against each other, thereby closing the outlet 17.

The tubular part preferably has an elongated form, with a length of at least three times the diameter of the rearward end of the catheter, and preferably at least five times said diameter, and most preferably at least ten times said diameter. Further, the length of said tubular part is preferably at least 30 mm, and most preferably at least 80 mm. Further, the tubular part preferably has an inner diameter which is at least twice the inner diameter of a lumen of the catheter. The inner diameter of the tubular part of the check valve arrangement is preferably wider at the outlet than at the inlet.

The tubular part is preferably connected to the rearward part of the catheter around its perimeter, and by means of at least one of the following methods: shrinkage, force fitting, welding and adhesive bonding.

The tubular part of the check valve arrangement is preferably formed from an plastic material. Further, the wall thickness is preferably less than 0.5 mm, and most preferably less than 0.3 mm, in order to be sufficiently flexible.

Figure 2:
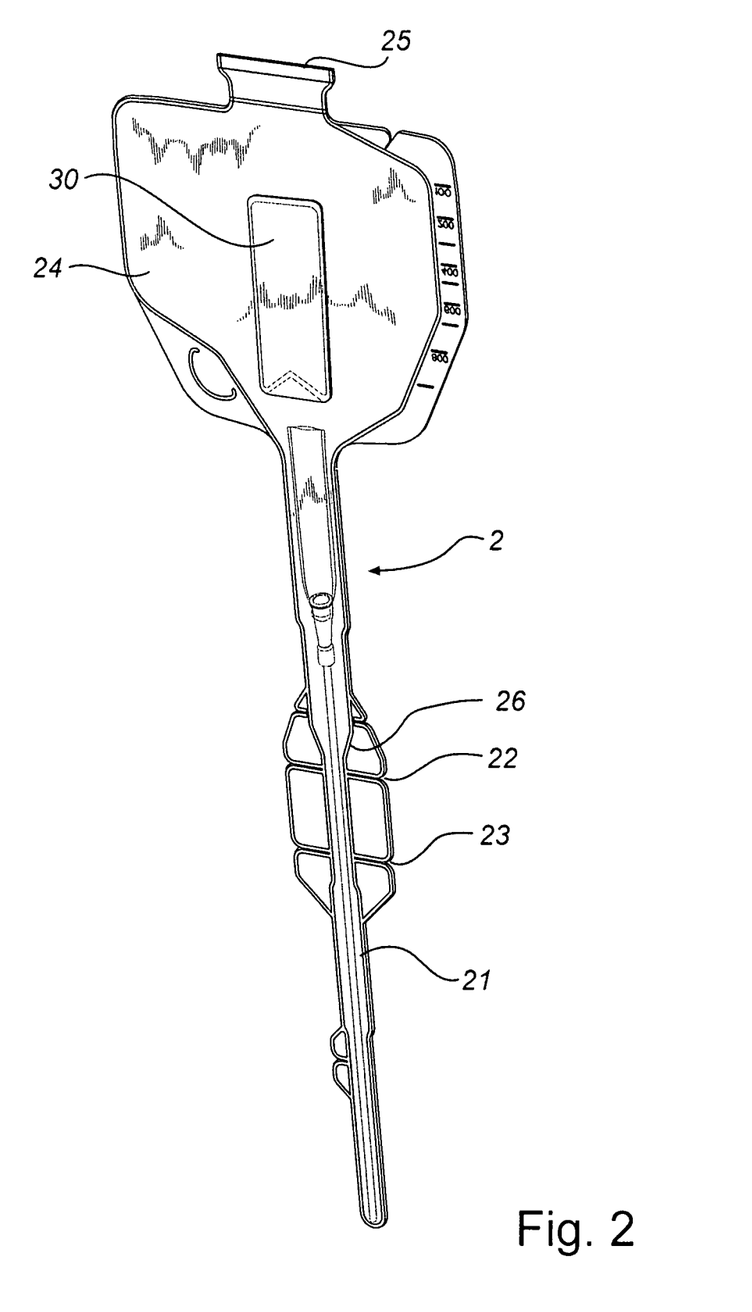
FIG. 2 illustrates a urinary catheter assembly comprising the urinary catheter of FIG. 1, according to one embodiment of the invention, in a closed state.

With reference to FIG, 2, a first embodiment of a catheter assembly comprises a wetting receptacle or receptacle 2, preferably of a transparent flexible plastics material, and a catheter 10 arranged therein. The receptacle 2 has an elongate pocket 21 at its forward end, and along the elongate pocket there is provided means 22, 23 for opening the receptacle, such as tear lines or, the like, as is per se well known in the art. Further opening means may be arranged at the forward or rearward end. The wetting receptacle 2 is adapted for accommodation of at least the insertable length of the catheter tube 12 in the elongate pocket 21.

The rearward end of the receptacle preferably forms a urine collection bag 24, which is in fluid connection with the elongate pocket 21. A rearward opening 25 may be provided for discharge of the urine from the urine collection bag. However, a discharge opening may also, alternatively or additionally, be provided on other parts of the receptacle, such as in various position on the urine collection bag. Such an opening may e.g. be formed as a tear line which may be manually torn open when the receptacle is to be opened.

The catheter assembly further comprises a hydrophilic urinary catheter 10, as is discussed in more detail in the foregoing.

The catheter assembly according to this embodiment also comprises a wetting fluid arranged at the rearward end. The wetting fluid is here provided separated from the hydrophilic surface of the catheter during storage, in a separate wetting fluid compartment 30. The wetting fluid is intended to wet the hydrophilic surface coating, thereby to produce the low-friction character of the same. A suitable wetting fluid for most hydrophilic coatings could typically be sterile water or saline. In the embodiments of e.g. FIG. 2, the wetting fluid is kept separated from the catheter in a compartment which is openable in order to enable activation of the catheter assembly. Thus, the activation is performed by opening the compartment and releasing the wetting fluid into the receptacle holding the catheter so that it comes into contact with the hydrophilic coating of the catheter. The wetting fluid compartment could be a separate container, or an integrated compartment of the receptacle. The compartment may be openable by means of pressing, tearing, piercing, twisting, etc, which is per se well-known in the art.

However, alternatively the wetting fluid could be arranged in direct contact with the hydrophilic coating, thus maintaining the coating in a constantly activated state (not shown), as is per se known in the art. Further, it is also possible to use an external supply of wetting fluid, such as water, whereby the receptacle is opened before activation, for introduction of the wetting fluid into the receptacle.

Figure 3:
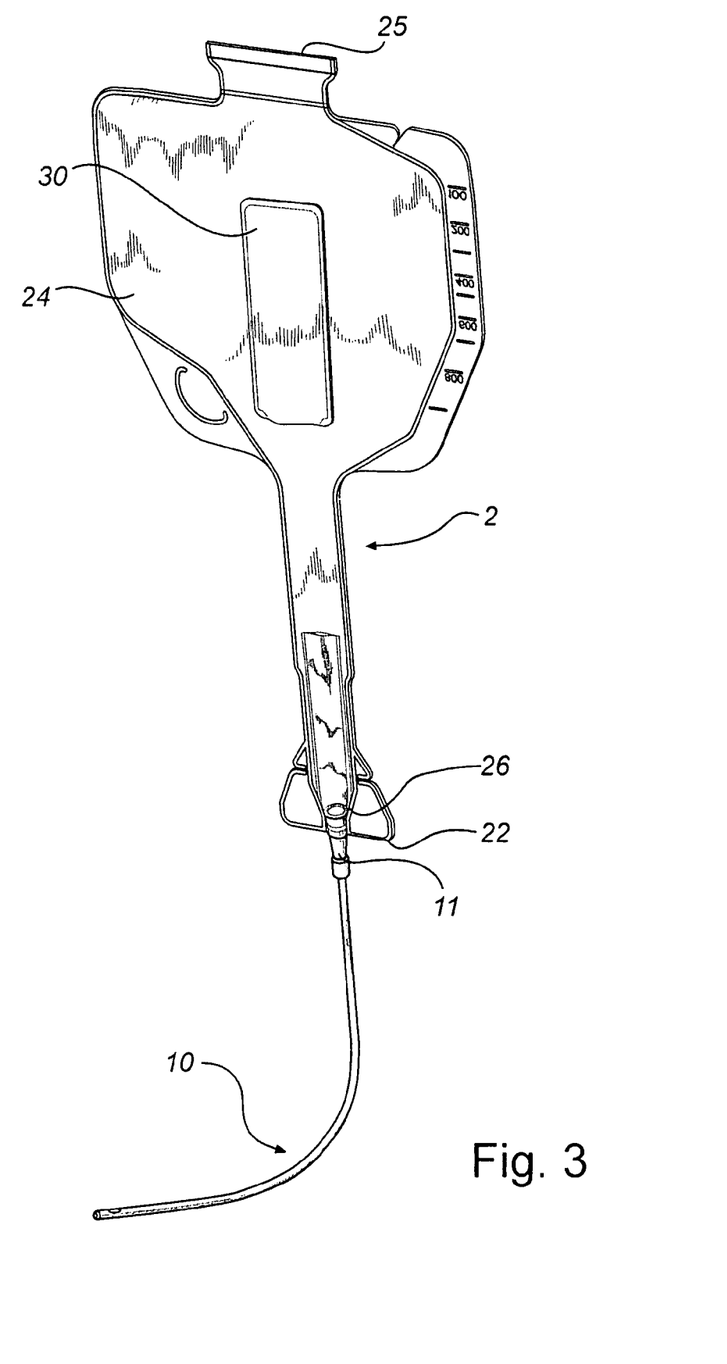
FIG. 3 illustrates the urinary catheter assembly of FIG. 2 in an opened state.

The above-discussed arrangement allows the catheter to be appropriately wetted during the initialization before use, allowing the wetting fluid to flow freely within the receptacle. After wetting, wherein the hydrophilic surface coating of the catheter is activated for use, the forward end of the receptacle may be opened, as is illustrated in FIG. 3, whereby the catheter may be moved out from the receptacle with the insertion end 14 first, in order to protrude from the receptacle, for insertion in the urethra of the patient. Preferably, the catheter is moved out from the receptacle to such an extent that the flared rearward end engages with a narrowing part 26 formed in the elongate pocket 21. Hereby, the flared rearward end of the catheter and the narrowing part of the elongated pocket preferably forms a sealed connection. In this position, the tubular part 15 functions as a one-way check-valve arrangement, preventing a reflux of collected urine through the catheter.

Many different alternative embodiments for the check-valve arrangement and the tubular part are feasible, and in the following some of these alternative embodiments will be discussed in some detail with reference to FIGS. 4-9. However, it is to be appreciated by those versed in the art that further combinations of these alternatives are also feasible, as well as other embodiments to form the tubular part of the check-valve arrangement.

In the above-discussed first embodiment, as illustrated in FIG. 1, the tubular part 15 comprises a two sheets 18A, 18B of a flexible material, being connected, e.g. by means of welding, along the edges, with connecting lines 19A and 19B extending essentially in the axial direction of the catheter, thereby forming the tubular part with two openings at the ends 16, 17. The use of two sheets makes the rearward opening prone to assume a relatively closed resting position, thereby enhancing the anti-reflux properties of the valve.

Figure 6:
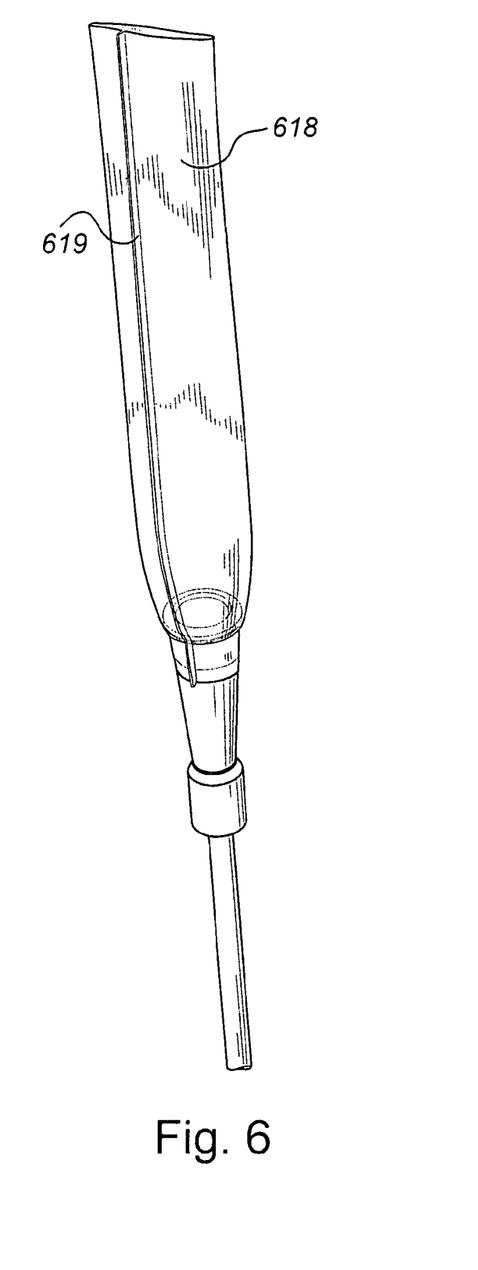
FIG. 6 illustrates the rearward end of a urinary catheter according to a further embodiment of the invention.

In an alternative embodiment, as illustrated in FIG. 6, the tubular part is made of a single sheet 618, which is bent to form a tubular shape, and is connected by welding or the like to form a connection line 619 extending essentially in the axial direction of the catheter. In this embodiment, the manufacturing of the tubular part can be facilitated, since only one single sheet of material need to be used to form the tubular part, and only one connection line need to be formed.

Figure 4:
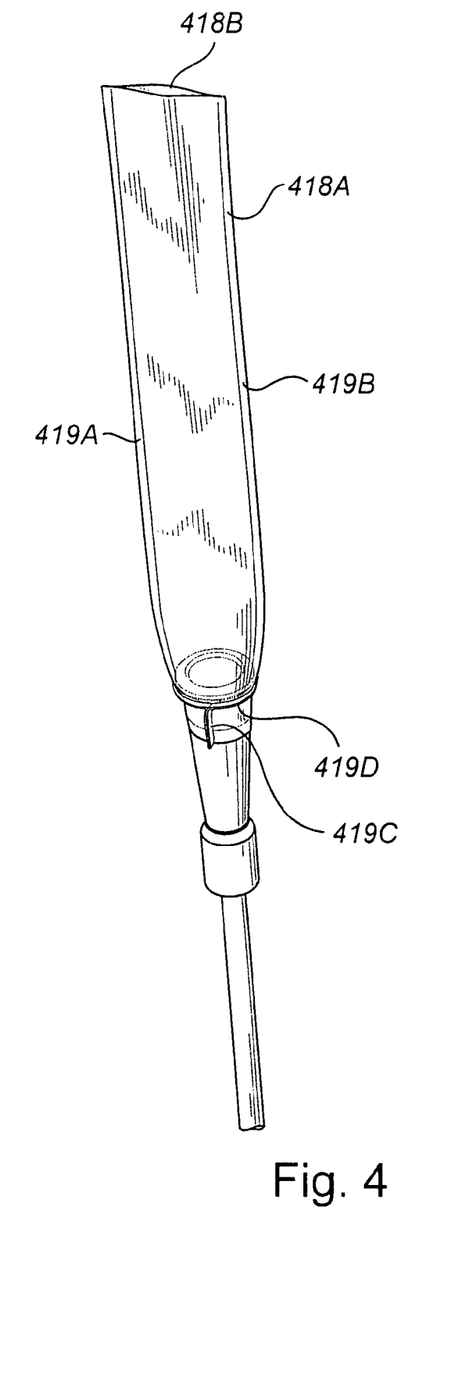
FIG. 4 illustrates the rearward end of a urinary catheter according to another embodiment of the invention.

In still another embodiment, illustrated in FIG. 4, the rearward end of the tubular part, being furthest away from the insertable part of the catheter, is formed from two sheets 418A, 418B, being connected together along two connection lines 419A, 419B, in the same way as in the embodiment of FIG. 3. However, the forward end of the tubular part, being closest to the insertable part of the catheter, is formed from a single sheet 418B of material, and connected by means of a single connection line 419C, in analogy to the embodiment discussed with reference to FIG. 6. Between the different ends, a transition region with transverse connection lines 419D may be provided. In this embodiment, the same advantages with respect to the rearward opening as in the embodiment of FIG. 3 is obtainable, and at the same time, the forward opening is easy to form and easy to connect to the rearward end of the catheter.

Figure 5:
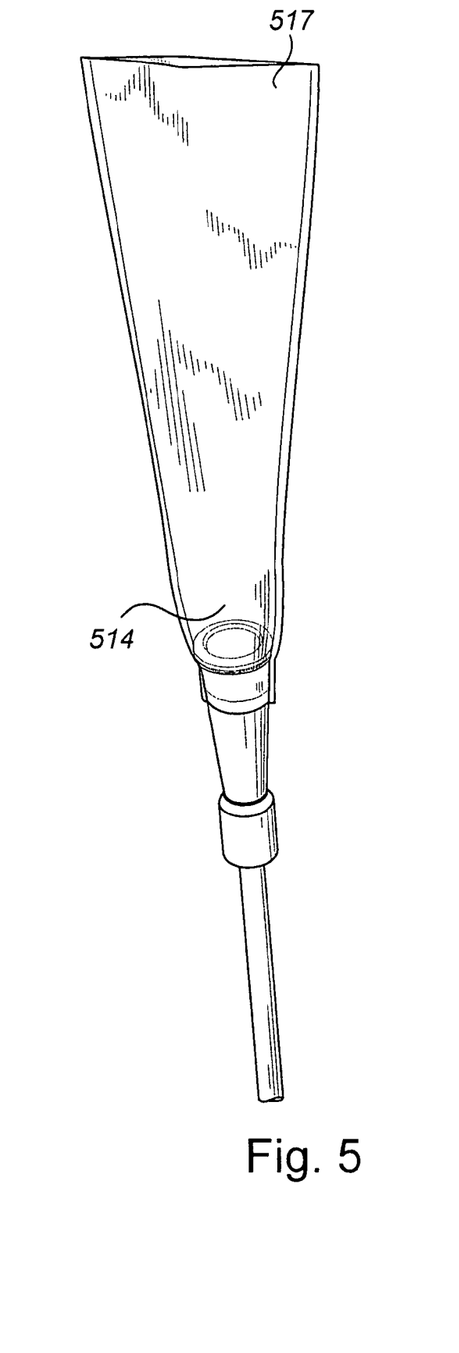
FIG. 5 illustrates the rearward end of a urinary catheter according to still another embodiment of the invention.

In the previously described embodiments the tubular part may be slightly narrower at the end being connected to the rearward part of the catheter than at the remained of the tubular part, even though this is not a requirement, and a constant width may be used as well. However, the width of the tubular part may also be gradually increasing over a part or the whole length of the tubular part. Such an embodiment is illustrated in FIG. 5, where tubular part is significantly narrower at the insertion end 514 than at the outlet end 517, and with a gradually transition of the width in the intermediate part. By such an arrangement, the flow resistance in the tubular part may be significantly lowered.

Figure 7:
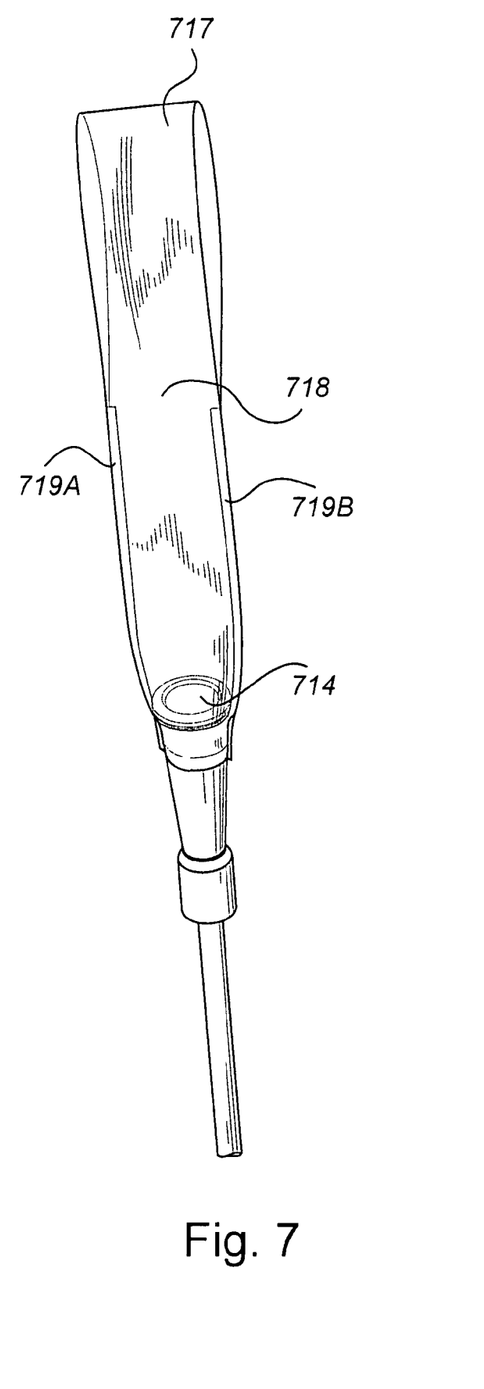
FIG. 7 illustrates the rearward end of a urinary catheter according to still another embodiment of the invention.

In the previously discussed embodiments, the tubular part is provided with one forward, inlet opening and one rearward, outlet opening. However, it is also possible to provide several outlet openings. Such an example is illustrated in FIG. 7, where the tubular part is formed from a single sheet 718 of flexible material, being folded at the rearward end 717, and being connected by connection lines 719A, 719B, extending essentially in the axial direction of the catheter, from the forward end 714 of the tubular part, and towards the rearward part 717, but not fully reaching the rearward part. Hereby, lateral openings are formed on each side of the tubular part. The check-valve of this embodiment is relatively easy to produce, and provides good anti-reflux properties.

Figure 8:
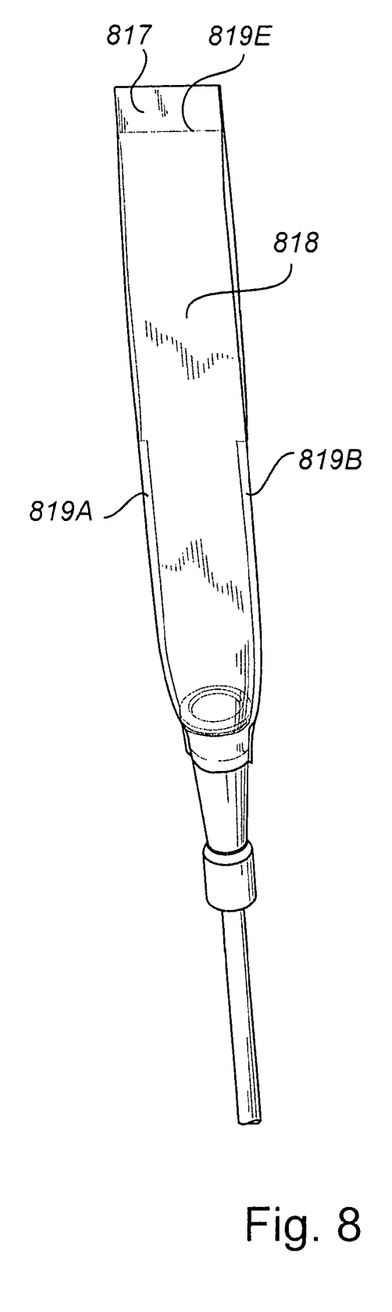
FIG. 8 illustrates the rearward end of a urinary catheter according to a further embodiment of the invention.

In a similar embodiment, illustrated in FIG. 8, a similar tubular part is formed with a single sheet 818 of material, and connecting lines 819A, 819B extending over a part of the length of the tubular part, leaving lateral openings close to the rearward end 817. However, in this embodiment, there is also provided a lateral connecting line 819E, such as a weld line, extending transversely over the tubular part close to the rearward end 817. Hereby, the lateral openings are brought to a nearly closed resting position, thereby providing enhanced anti-reflux properties.

Figure 9:
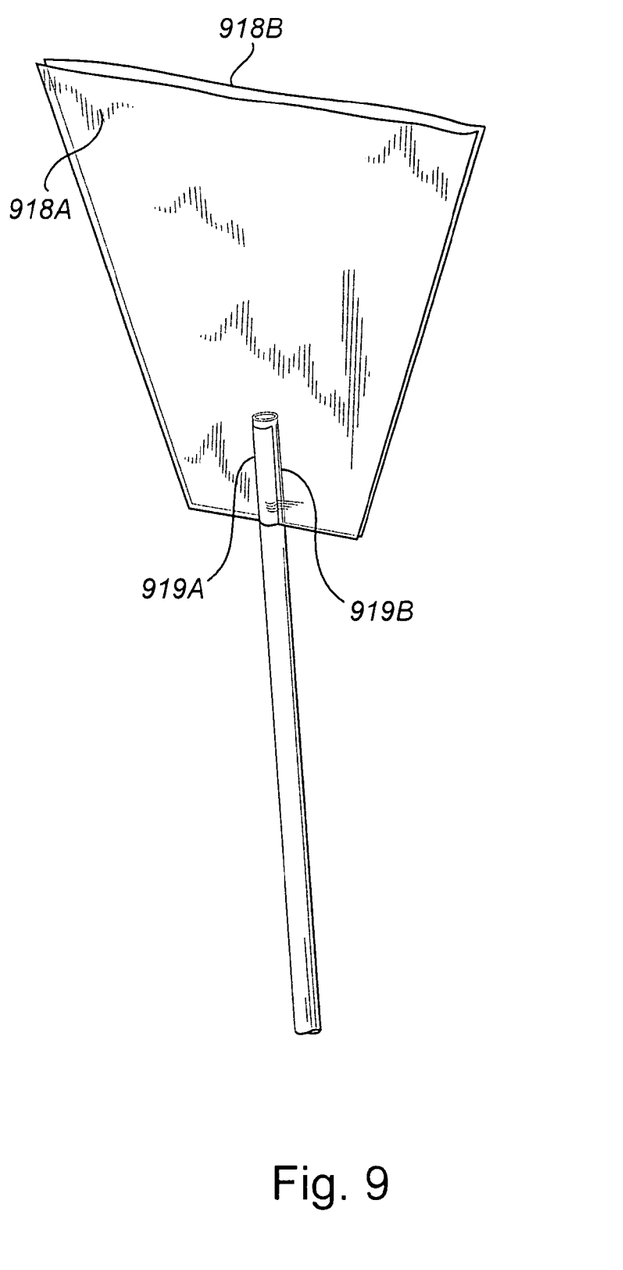
FIG. 9 illustrates the rearward end of a urinary catheter according to still another embodiment of the invention.
Figure 10:
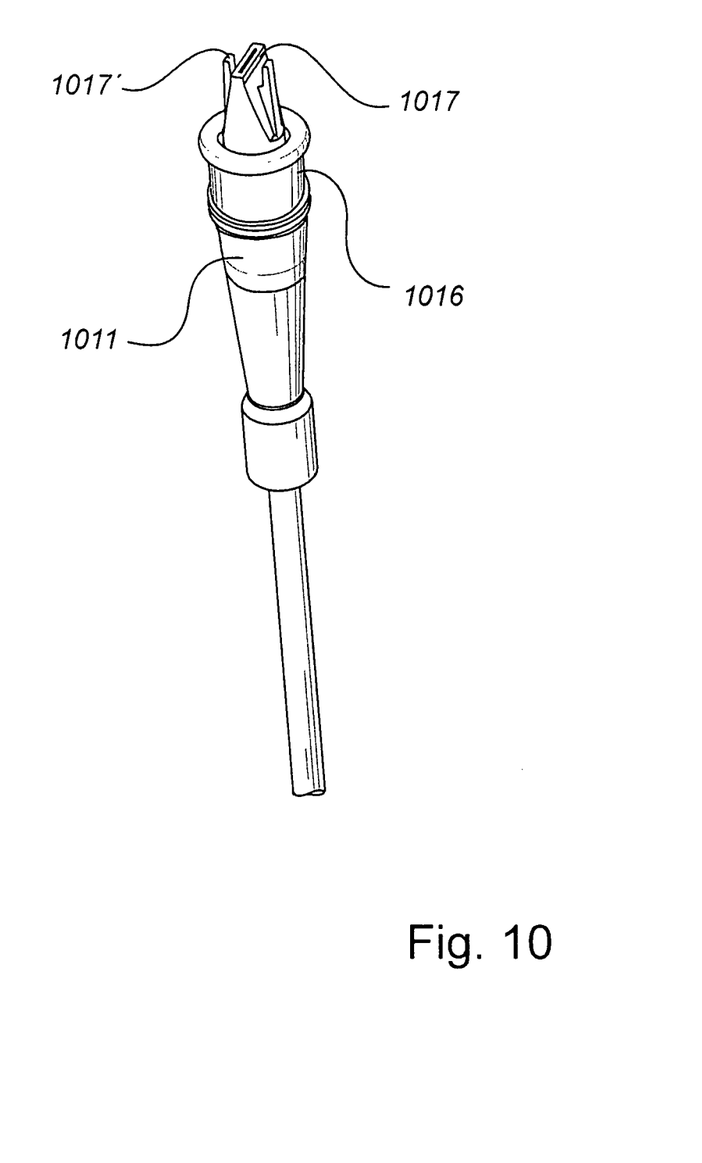
FIG. 10 illustrates the rearward end of a urinary catheter according to still another embodiment of the invention.

In a further embodiment, as illustrated in FIG. 9, there is provided a tubular part with a relatively narrow tubular opening. This tubular part comprises two sheets 918A, 918B of a flexible material, being connected only close to the forward end, in the vicinity of the rearward end of the catheter. A tubular opening is formed by means of two connecting lines 919A, 919B, such as weld lines, arranged on each side of the rearward end of the catheter, and having a relatively short extension. Preferably, the connecting lines have essentially the same extension as the rearward end of the catheter in between the flexible material sheets. Hereby, a very wide opening is formed, essentially extending around the whole outer edge of the sheets. In this embodiment, the sheets are held together relatively loosely, thereby providing a very flexible check-valve arrangement, but still enabling adequate anti-reflux properties to be obtained. Still a further embodiment of the invention is illustrated in FIG. 10. In this embodiment, the tubular part comprises a unit made in one piece, e.g. by moulding, and made of a flexible material, such as silicone. The tubular part of this embodiment comprises a cylindrical base part 1017, with a diameter essentially corresponding to the end of the rearward part 1011 of the catheter. Hereby, the tubular part may be connected to the end surface of the rearward part by means of e.g. gluing or welding. Further, the tubular part comprises an outlet opening part 1017 formed in the shape of a duck bill, forming a slit shaped opening at the end. Hereby, a one-way valve is formed, since the duck bill end will allow passage of urine coming through the catheter, but will be automatically closed for passage of urine from the outside and into the catheter. Stabilizing tongues 1017' may be formed so that they extend outside of the duck bill opening. These stabilizers will allow a more smooth and stable operation of the duck bill, and will also prevent harmonic oscillations from occurring during use, as well as possibly incurred noise caused by such oscillations.

The invention has now been discussed in relation to different embodiments. However, it should be appreciated by those versed in the art that several further alternatives are possible. For example, the features of the different embodiments discussed above may naturally be combined in many other ways.

Still further, it is possible to arrange the wetting fluid container in many different ways. For example, the container may be a separate container, but forming part of the assembly. Such a wetting fluid container may be arranged completely inside the receptacle, partly inside the receptacle, or completely outside the receptacle. Alternatively, the wetting fluid container may be an integrated compartment of the receptacle. This compartment may be separated from the compartment housing the insertable part of the catheter, or be integrated with such a compartment. In the latter case, the catheter may be maintained in a wetted, activated state.

Further, the wetting fluid container may be arranged in various parts of the receptacle, in any suitable location in the assembly. In case the wetting fluid is arranged separately from the insertable part of the catheter, the separation wall or joint could e.g. be a breakable or peelable membrane wall, but alternative embodiments are naturally feasible, such as various types of detachable or openable caps or closings. The wetting fluid container may be arranged to be discharged upon application of a twist, a compression, a pull or the like on the fluid container. Preferably the wetting fluid may be discharged without breaking or rupturing the receptacle, even though this may not be necessary, depending on the intended use, etc.

Many different materials could also be used for the different parts of the catheter assembly.

The tubular part may be connected to the catheter in various ways, and may be formed from many different materials, may take many different shapes, etc, as long as the above-discussed functionality is still obtained.

It will be appreciated by those versed in the art that several such alternatives similar to those described above could be used without departing from the spirit of the invention, and all such modifications should be regarded as a part of the present invention, as defined in the appended claims.

The invention claimed is:

1. A urinary catheter assembly for insertion into a body opening of a user, comprising:
 a catheter having an insertion end and a rearward end;
 a wetting fluid compartment adapted to release a wetting fluid to come in contact with and form a low friction surface of the catheter portion of the assembly prior to insertion of the catheter assembly into the body opening of the user;
 the rearward end of the catheter forming a connector for the catheter, wherein the exterior of the rearward end has a frusto-conical shape, and the external diameter of said rearward end increases in a direction away from the catheter insertion end,
 a one way check valve arrangement, wherein said check valve arrangement comprises a tubular part of a flexible material, said tubular part of a flexible material being connected to the frusto-conical rearward end of the catheter, so that an inner surface of the tubular part of a flexible material is adhered to an external surface of the frusto-conical rearward end of the catheter, and so that the tubular part of a flexible material extends past the rearward end in a direction opposite to the insertion end and is adapted to close when subjected to a fluid in a wetting receptacle that presses against the tubular part of flexible material to substantially limit the flow through the catheter to a single direction from the insertion end to the rearward end,
 wherein the wetting receptacle encompasses the wetting fluid compartment, the catheter and the one way check valve, and which is adapted to be opened prior to insertion of the catheter into the body opening of the user, and
 wherein the tubular part of the check valve arrangement has an inner diameter which is at least twice the inner diameter of a lumen of the catheter.

2. The urinary catheter according to claim 1, wherein the tubular part comprises two openings, one of which is sealingly connected to the rearward end of the catheter, and the other presenting an open end opposite to said sealingly connected end.

3. The urinary catheter according to claim 1, wherein the check valve arrangement has an inlet at its attachment to the rearward end, and an outlet at the opposite end of the tubular part, wherein said inlet remains substantially open for passage of fluids there through, and said outlet being biased to closure after discharge of fluids through said outlet, thereby substantially limiting the flow to a single direction from said inlet to said outlet.

4. The urinary catheter according to claim 1, wherein the tubular part has an elongated form, wherein the length of the tubular part is in a range from three times the diameter of the rearward end of the catheter to ten times said diameter.

5. The urinary catheter according to claim 1, wherein the tubular part has an elongated form, wherein the length of said tubular part is in a range from 30 mm to 80 mm.

6. The urinary catheter according to claim 1, wherein the check valve arrangement has a perimeter attached along an exterior periphery of the rearward end of the catheter.

7. The urinary catheter according to claim 1, wherein the tubular part is connected to said rearward end by means of at least one of the following methods: shrinkage, force fitting, welding and adhesive bonding.

8. The urinary catheter according to claim 1, wherein the insertable length of the catheter is provided with a hydrophilic surface coating providing low-friction surface character of the catheter by treatment with a wetting fluid.

9. The urinary catheter according to claim 1, wherein the tubular part of the check valve arrangement is formed from a plastic material.

10. The urinary catheter according to claim 1, wherein the tubular part of the check valve arrangement has a wall thickness less than 0.5 mm.

11. The urinary catheter according to claim 1, wherein the inner diameter of the tubular part of the check valve arrangement is wider at the outlet than at the inlet, wherein the outlet inner diameter is at least twice the inlet inner diameter.

12. The urinary catheter of claim 1, wherein the wetting receptacle forms a urine collection bag; and
wherein the catheter has a storage position in which the catheter is fully contained within the wetting receptacle, and an operative position in which the catheter is located outside of the wetting receptacle, and is adapted to move between the storage position and the operative position via an opening in the wetting receptacle; and
wherein the flared rearward end is adapted to engage with the wetting receptacle to form a sealed connection therebetween; and
wherein the one-way check valve is connected to the catheter for concurrent movement with the catheter.

13. A urinary catheter assembly for insertion into a body opening of a user, comprising
a urinary catheter having an insertion end and a rearward end, and a wetting receptacle, arranged to accommodate said catheter;
a wetting fluid compartment adapted to release a wetting fluid to come in contact with and form a low friction surface of the catheter portion of the assembly prior to insertion of the catheter assembly into the body opening of the user;
wherein the rearward end forms a connector for the catheter, the exterior of the rearward end of the catheter has a frusto-conical shape, and the external diameter of which increases in a direction away from the catheter insertion end;
a one way check valve arrangement, wherein said check valve arrangement comprises a tubular part of a flexible material, said tubular part of flexible material being connected to the frusto-conical exterior of the rearward end of the catheter, so that an inner surface of the tubular part of flexible material is directly connected to an exterior surface of said frusto-conical rearward end, the tubular part of flexible material extending past the rearward end in a direction opposite to the insertion end and is adapted to close when subjected to a fluid in the wetting receptacle that presses against the tubular part of flexible material to substantially limit the flow to a single direction from the insertion end to the rearward end,
wherein the wetting receptacle encompasses the wetting fluid compartment, the catheter and the one way check valve, and which is adapted to be opened prior to insertion of the catheter into the body opening of the user, and
wherein an inner diameter of the tubular part of the check valve arrangement is wider at the outlet than at the inlet, wherein the outlet inner diameter is at least twice the inlet inner diameter.

14. The urinary catheter assembly according to claim 13, wherein the tubular part comprises two openings, one of which is sealingly connected to the rearward end of the catheter, and the other presenting an open end opposite to said sealingly connected end.

15. The urinary catheter assembly according to claim 13, wherein the tubular part has an inlet at its attachment to the rearward end, and an outlet at the opposite end of the tubular part, wherein said inlet remains substantially open for passage of fluids there through, and said outlet being biased to closure after discharge of fluids through said outlet, thereby substantially limiting the flow to a single direction from said inlet to said outlet.

16. The urinary catheter assembly according to claim 13, wherein the wetting receptacle is also a urine collection bag.

17. The urinary catheter assembly according to claim 13, wherein at least a part of the catheter is provided with a hydrophilic surface coating.

18. The urinary catheter assembly according to claim 17, wherein the wetting receptacle has an elongate pocket, defining a wetting fluid receiving area, which accommodates the insertable length of said urinary catheter.

19. The urinary catheter assembly according to claim 17, wherein the wetting fluid compartment comprises a wetting fluid container, the wetting fluid container containing a wetting fluid and being openable to enable the wetting fluid to be discharged for wetting of the urinary catheter.

20. The urinary catheter assembly according to claim 18, wherein the elongate pocket of the wetting presents an openable forward end, thereby enabling at least the insertable length of the urinary catheter to be projected through an opening, wherein said opening being arranged to engage with the rearward end of the catheter upon projection, thereby substantially sealing the connection.

21. The urinary catheter assembly according to claim 13, wherein the tubular part has an elongated form, wherein the length of said tubular part is in a range from three times the diameter of the rearward end of the catheter to ten times said diameter.

22. The urinary catheter according to claim 13, wherein the tubular part is connected to the rearward part by means of at least one of the following methods: shrinkage, force fitting, welding and adhesive bonding.

23. The urinary catheter according to claim 13, wherein the tubular part of the check valve arrangement has a wall thickness less than 0.5 mm.

24. The urinary catheter assembly of claim 13, wherein the wetting receptacle forms a urine collection bag; and
wherein the catheter has a storage position in which the catheter is fully contained within the wetting receptacle, and an operative position in which the catheter is located outside of the wetting receptacle, and is adapted to move between the storage position and the operative position via an opening in the wetting receptacle; and
wherein the flared rearward end is adapted to engage with the wetting receptacle to form a sealed connection therebetween; and
wherein the one-way check valve is connected to the catheter for concurrent movement with the catheter.

25. A method for manufacturing a urinary catheter assembly for insertion into a body opening of a user with a one way check valve arrangement, comprising the steps:
providing a urinary catheter having an insertion end and a rearward connector end and a wetting fluid compartment adapted to release a wetting fluid to come in contact with and form a low friction surface of the catheter portion of the assembly prior to insertion of the catheter assembly into the body opening of the user, wherein the exterior of the rearward connector end has a frusto-conical shape, and the external diameter of said rearward connector end increases in a direction away from the catheter insertion end;
providing a tubular part of a flexible material;
connecting an inner surface of said tubular part of a flexible material to an external surface of said frusto-conical rearward connector end of the urinary catheter in such a way that the tubular part extends past the rearward connector end in a direction opposite to the insertion end of the catheter, and is adapted to close when subjected to a fluid in a wetting receptacle that presses against the tubular part of a flexible material for provision of said check valve arrangement;

wherein the wetting receptacle encompasses the wetting fluid compartment, the catheter and the one way check valve, and is adapted to be opened prior to insertion of the catheter into the body opening of the user, and wherein the inner diameter of the tubular part is wider at the outlet than at the inlet, wherein the inner outlet diameter is at least twice the inner inlet diameter.

26. The method according to claim 25, wherein the tubular part comprises two openings, one of which is sealingly connected to the rearward end of the catheter, and the other presents an open end opposite to said sealingly connected end.

27. The method according to claim 25, wherein the check valve arrangement has an inlet at its attachment to the rearward end, and an outlet at the opposite end of the tubular part, wherein said inlet remains substantially open for passage of fluids there through, and said outlet being biased to closure after discharge of fluids through said outlet, thereby substantially limiting the flow to a single direction from said inlet to said outlet.

28. The method according to claim 25, wherein the tubular part has an elongated form, wherein the length of the tubular part is in a range from three times the diameter of the rearward end of the catheter to ten times said diameter.

29. The method according to claim 25, wherein the tubular part is connected to said rearward end by means of at least one of the following methods: shrinkage, force fitting, welding and adhesive bonding.

30. The method according to claim 25, comprising the further step of placing the urinary catheter in the wetting receptacle, arranged to accommodate said urinary catheter.

31. The method according to claim 25, wherein a perimeter of the tubular part is attached along an exterior periphery of the rearward end of the urinary catheter.

32. The method according to claim 25, wherein the tubular part is formed from an elastomeric/plastic material.

33. The method according to claim 25, wherein the tubular part has a wall thickness less than 0.5 mm.

34. The method of manufacturing a urinary catheter assembly of claim 25, wherein the wetting receptacle forms a urine collection bag; and wherein the catheter has a storage position in which the catheter is fully contained within the wetting receptacle, and an operative position in which the catheter is located outside of the wetting receptacle, and is adapted to move between the storage position and the operative position via an opening in the wetting receptacle; and wherein the flared rearward end is adapted to engage with the wetting receptacle to form a sealed connection therebetween; and wherein the one-way check valve is connected to the catheter for concurrent movement with the catheter.

* * * * *